United States Patent
Wu et al.

(10) Patent No.: US 9,150,482 B2
(45) Date of Patent: Oct. 6, 2015

(54) GLP-1 POTENTIATORS FROM HEDYCHIUM CORONARIUM AND THEIR APPLICATIONS

(71) Applicants: Rey-Yuh Wu, New Taipei (TW);
Hui-Ling Chen, New Taipei (TW);
Yu-Yuan Wu, New Taipei (TW);
Jiann-Jyh Huang, New Taipei (TW);
Shoei-Sheng Lee, Taichung (TW);
K-Lim King, New Taipei (TW)

(72) Inventors: Rey-Yuh Wu, New Taipei (TW);
Hui-Ling Chen, New Taipei (TW);
Yu-Yuan Wu, New Taipei (TW);
Jiann-Jyh Huang, New Taipei (TW);
Shoei-Sheng Lee, Taichung (TW);
K-Lim King, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

(21) Appl. No.: 13/912,102

(22) Filed: Jun. 6, 2013

(65) Prior Publication Data
US 2013/0331323 A1 Dec. 12, 2013

Related U.S. Application Data

(60) Provisional application No. 61/656,393, filed on Jun. 6, 2012.

(51) Int. Cl.
*A61K 38/26* (2006.01)
*A61K 31/397* (2006.01)
(Continued)

(52) U.S. Cl.
CPC .............. *C07C 47/225* (2013.01); *A61K 31/11* (2013.01); *A61K 31/351* (2013.01);
(Continued)

(58) Field of Classification Search
CPC .... C07C 47/225; C07C 47/46; C07C 47/267; A61K 31/365; A61K 31/11; A61K 31/351; A61K 31/357; A61K 31/397; A61K 31/337; A61K 38/26; A61K 45/06; A61K 36/9068; A61K 2300/00; C07D 321/04; C07D 305/14; C07D 205/12; C07D 309/30
USPC .............. 514/7.2, 210.16, 449, 450; 548/950; 549/346, 347, 367, 420, 510; 568/445
See application file for complete search history.

(56) References Cited

FOREIGN PATENT DOCUMENTS

JP 09176083 * 7/1997

OTHER PUBLICATIONS

Christensen et al, Activation of the nuclear receptor PPARr by metabolites isolated from sage,2010, Journal of Ethnopharmacology, 132,(1), p. 127-133.*

(Continued)

*Primary Examiner* — T. Victor Oh
(74) *Attorney, Agent, or Firm* — Osha Liang LLP

(57) ABSTRACT

A compound for controlling blood glucose level has a structure shown in Formula I:

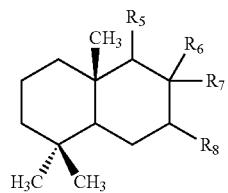

Formula I wherein R5-R8 are as defined herein. A method for controlling blood glucose level includes administering to a subject in need thereof a compound of Formula I. The method further includes administering to the subject a GLP-1 receptor ligand. The compound and the GLP-1 receptor ligand may be administered together. The compound may be Galanal A or Galanal B. The GLP-1 receptor ligand may be GLP-1 or exendin-4.

8 Claims, 8 Drawing Sheets

(51) Int. Cl.
   *A61K 31/335*   (2006.01)
   *C07C 321/00*   (2006.01)
   *C07C 45/00*    (2006.01)
   *C07C 47/225*   (2006.01)
   *C07D 309/30*   (2006.01)
   *C07D 321/04*   (2006.01)
   *C07C 47/267*   (2006.01)
   *C07D 205/12*   (2006.01)
   *C07D 305/14*   (2006.01)
   *A61K 31/11*    (2006.01)
   *A61K 31/351*   (2006.01)
   *A61K 31/357*   (2006.01)
   *C07C 47/46*    (2006.01)
   *A61K 36/9068*  (2006.01)
   *A61K 45/06*    (2006.01)
   *A61K 31/365*   (2006.01)
   *C07C 47/277*   (2006.01)
   *A61K 31/337*   (2006.01)

(52) U.S. Cl.
   CPC ............ *A61K 31/357* (2013.01); *A61K 31/365* (2013.01); *A61K 31/397* (2013.01); *A61K 36/9068* (2013.01); *A61K 38/26* (2013.01); *A61K 45/06* (2013.01); *C07C 47/267* (2013.01); *C07C 47/277* (2013.01); *C07C 47/46* (2013.01); *C07D 205/12* (2013.01); *C07D 305/14* (2013.01); *C07D 309/30* (2013.01); *C07D 321/04* (2013.01); *A61K 31/337* (2013.01); *C07C 2102/26* (2013.01); *C07C 2103/30* (2013.01)

(56) References Cited

OTHER PUBLICATIONS

Duker-Eshun et al , Antiplasmodial activity of Labdanes from Aframomum latifolium and Aframomum sceptrum,2002, Planta Medica , 68(7), p. 642-644.*

Pljevljakusic et al , chemical Properties of the cultivated *Sideritis raeseri* Boiss. & Heldr. subsp. *raeseri*, 2010, Food Chemistry, 124(1), p. 226-233.*

Henderson et al, A concise Diels-alder strategy for the Asymmetric synthesis of (+)-albicanol, (+)albicanyl acetate, (+)-dihydrodrimenin, and (−)-dihydroisodrimeninol, 2009, Oraganic Letters, 11(15), p. 3178-3181.*

Zhou et al, Bioactive Labdane Diterpenoids rom Renealmia alpinia collected in the Suriname Rainforest, Journal of Natural Products, 1997, 60, p. 1287-1293.*

Margaros et al , Synthesis of Chinensines A-E, Journal of Organic Chemistry , 2007, 72, p. 4826-4831.*

* cited by examiner

Semi-Synthesis of GLP-1 Potentiators (a) Compound 1

(b) Compound 2

(a)

(b)

(c)

| P value | 0 | 30 | 60 | 90 |
|---|---|---|---|---|
| G1-G2 | 0.978513173 | 0.005463081 | 0.1046699 | 0.196604 |
| G1-G3 | 0.849088318 | 0.009327189 | 0.1202749 | 0.0158897 |
| G1-G4 | 0.934629578 | 0.00013562 | 0.0038101 | 0.0017211 |

Reduction in Blood Glucose (%)

| | Total AUC | AUC from 0 min. |
|---|---|---|
| G2 | 8.10% | 41.19% |
| G3 | 8.21% | 45.11% |
| G4 | 13.87% | 71.39% |

GLP-1 POTENTIATORS FROM HEDYCHIUM CORONARIUM AND THEIR APPLICATIONS

BACKGROUND OF THE INVENTION

1. Technical Field of the Invention

The present invention relates to new uses of compounds, particularly a diterpenoid Galanal B, in the regulation of blood glucose levels.

2. Background

Glucagon-like peptide-1 (GLP-1) analogues are a new class of hypoglycemic agents. GLP-1 is a member of the incretin family, which comprises gastrointestinal hormones that help control blood glucose levels after meals. GLP-1 exerts its functions by specific binding to GLP-1 receptor. GLP-1 receptor (GLP-1R) is widely distributed. In addition to pancreatic tissue, GLP-1 receptor is also distributed in the brain, lung, heart, kidney, etc. The wide distribution of this receptor contributes to the wide range of its functions.

GLP-1 bind specifically to the GLP-1 receptor on the pancreatic beta cells. Activation of GLP-1R leads to stimulation of the adenylyl cyclase pathway, which eventually leads to increased insulin synthesis and release. In addition to the increased insulin synthesis and release, GLP-1 binding to its receptor also inhibits the production of glucagon and maintains constant levels of blood glucose after meals. Furthermore, GLP-1 also has a neuron regulatory function, which can delay gastric emptying and reduce appetite. At the same time, the hypoglycemic effect of GLP-1 is self-limiting and will not result in hypoglycemia (i.e., will not result in over reduction in blood glucose levels). These properties are beneficial for diabetes controls. Therefore, drugs having GLP-1-like activities are ideal for diabetes controls and treatments. Accordingly, search for GLP-1 analogs has become a research focus for new drug developments.

However, GLP-1 is a peptide and is rapidly degraded by DPP-IV (dipeptidyl peptidase IV) in vivo, leading to loss of its biological activities. The in vivo half-life of GLP-1 is less than 2 min, necessitating continuous intravenous infusion or continuous subcutaneous injection to maintain its effects. This property greatly limits the clinical applications of GLP-1. Therefore, in recent years, there have been great efforts focusing on the research and development of long-lasting GLP-1 analogs and DPP-N inhibitors.

Currently available GLP-1 analogs, including Byetta® (Exenatide; Amylin Pharmaceuticals, San Diego, Calif.) and Victoza® (liraglutide; Novo Nordisk, Denmark), can effectively control blood glucose levels, without causing hypoglycemia, in type II diabetes patients who did not respond to other oral blood glucose lowering medications. The studies found that these GLP-1 analogues can reduce patients' body weights and control blood glucose at more stable levels. In addition, these GLP-1 analogs can maintain, and may even improve, the basal metabolisms and post glucose-stimulation beta cell functions in type II diabetic patients, and delay disease progression.

To date, research on GLP-1 analogs is mainly focused on peptide analogs or regulators. Because peptide drugs cannot be given by oral administration and they can be easily degraded, it would be desirable to have other types of drugs that have activities similar to GLP-1 analogs.

SUMMARY OF INVENTION

One aspect of the invention relates to compounds or compositions for controlling blood glucose levels. In some embodiments, a compound of the invention is a galanal analog having a structure shown in Formula I:

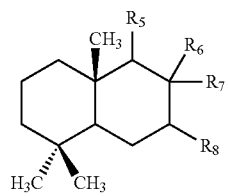

Formula I wherein $R_8$ is H, —OH, or an alkoxy (—O—R'), preferably, $R_8$ is H or —OH, and more preferably, $R_8$ is H;

$R_5$ is an alkyl (preferably, $C_1$-$C_{10}$ alkyl; more preferably $C_3$-$C_7$ alkyl) or an alkenyl containing one or more double bonds (preferably, $C_2$-$C_{10}$ alkenyl; more preferably, $C_3$-$C_7$ alkenyl), wherein the alkyl or alkenyl is straight-chained or branched and is optionally substituted with one or more substituents selected from —OR', —NR'R", —SR', oxo (═O), thioxo (═S), —CONR'R", —CN, —CO$_2$R', or —CR'R"OH, wherein R' and R" are independently H, $C_1$-$C_6$ alkyl, $C_2$-$C_6$ alkenyl, $C_3$-$C_{10}$ cycloalkyl or $C_6$-$C_{10}$ aryl; or $R_5$ contains a 5-, 6- or 7-membered ring that is a cycloalkyl or cycloalkenyl ring or a heterocyclic ring containing one or more hetero atoms selected from N, O, or S, wherein the 5-, 6-, or 7-membered ring is optionally substituted with one or more substituent selected from —OR', —NR'R", —SR', oxo (═O), thioxo (═S), —CONR'R", —CN, —CO$_2$R', or —CR'R"OH, wherein R' and R" are as defined above; and $R_6$ and $R_7$ are independently selected from H (provided that $R_6$ and $R_7$ are not both H), an alkyl (preferably, $C_1$-$C_{10}$ alkyl; more preferably $C_1$-$C_3$ alkyl) or an alkenyl containing one or more double bonds (preferably, $C_2$-$C_{10}$ alkenyl; more preferably, $C_3$-$C_5$ alkenyl), wherein the alkyl or alkenyl is a straight-chained or branched and is optionally substituted with one or more substituents selected from —OR', —NR'R", —SR', oxo (═O), thioxo (═S), —CONR'R", —CN, —CO$_2$R', or —CR'R"OH, wherein R' and R" are as defined above; or $R_6$ and $R_7$ jointly form an alkenyl (preferably, $C_1$-$C_3$ alkenyl with a double-bond linking to the common carbon atom on the ring; more preferably, ═CH$_2$);

or wherein $R_8$ is H, —OH, or an alkoxy (—O—R'), preferably, $R_8$ is H or —OH, and more preferably, $R_8$ is H;

$R_7$ is a formyl (—CHO), and $R_5$ and $R_6$ jointly form a ring, which is a 5, 6 or 7-membered ring made of C, O, N, or S atoms or a combination thereof, wherein the ring contains 0 or 1 double bond, and wherein the ring is optionally substituted with one or more alkyl side chains of 1-10 carbons ($C_1$-$C_{10}$), preferably 1-5 carbons ($C_1$-$C_5$), and wherein the ring and/or the one or more alkyl side chains independently are optionally substituted with one or more substituents selected from —OR', —NR'R", —SR', oxo (═O), thioxo (═S), —CONR'R", —CN, —CO$_2$R', or —CR'R"OH, wherein R' and R" are as defined above.

In some preferred embodiments, the compound may have a structure shown in Formula II (i.e., $R_6$ and $R_7$ jointly form ═CH$_2$ in Formula I):

Formula II

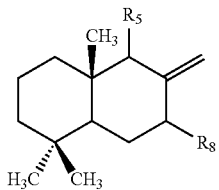

wherein $R_5$ and $R_8$ are as defined above.

In some preferred embodiments, the compound may have a structure shown in Formula (A) or (B):

(A)

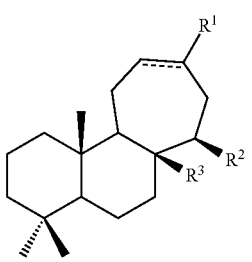

(B)

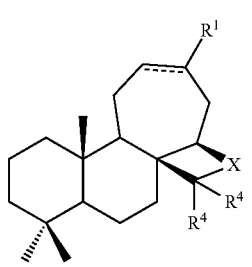

wherein $R^1$ is —CONR'R", —CN, —CO$_2$R', or —CR'R"OH; $R^2$ is —OR' or —NR'R"; $R^3$ is —CHO, —CH$_2$OR', or —CO$_2$R'; $R^4$ are both —H or together form =O; X is —O— or NR', wherein R' and R" are as defined above.

In some embodiments, the galanal analogs may comprise one or more of the following compounds, which may be synthesized or isolated from wild ginger flower extracts:

1B

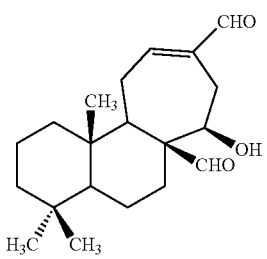

1A

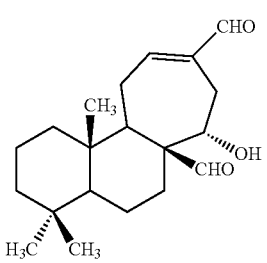

2

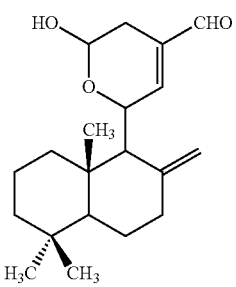

3

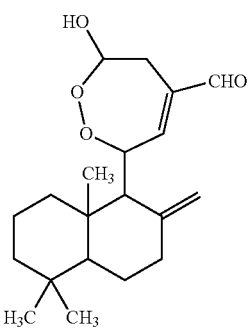

4

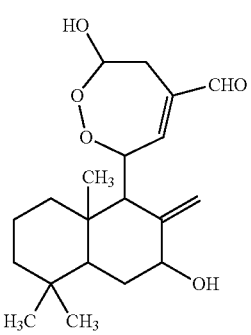

5

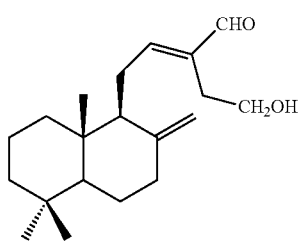

6

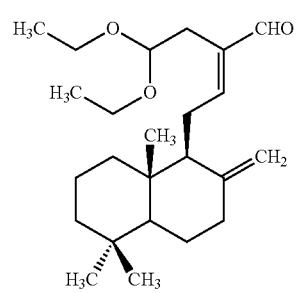

Wherein compound 1A is Galanal A, compound 1B is Galanal B; compound 2 is 11-hydroxy-8(17),12(E)-labda-dien-15,16-dial 11,15-hemiacetal; compound 3 is Coronarin B, compound 4 is 7β-Hydroxycoronarin B; compound 5 is (E)-labda-8(17),12-diene-15-ol-16-al; and compound 6 is (E)-15,15-diethoxylabda-8(17),12-dien-16-al.

One aspect of the invention relates to methods for controlling blood glucose levels. A method in accordance with one embodiment of the invention includes administering to a subject in need thereof a compound of Formula I or II. The compound may be Galanal A or Galanal B. The method may further include administering to the subject a GLP-1 receptor ligand. The GLP-1 receptor ligand may be GLP-1 or exendin-4. The compound and the GLP-1 receptor ligand may be administered sequentially or simultaneously.

Some embodiments of the invention may include administering to a subject in need thereof a compound of Formula (A) or (B). The method may further include administering to the subject a GLP-1 receptor ligand. The GLP-1 receptor ligand may be GLP-1 or exendin-4. The administering of the compound and the GLP-1 receptor ligand may be at the same time or in sequences.

Other aspects and advantages of the invention will be apparent from the following description and the appended claims.

BRIEF DESCRIPTION OF DRAWINGS

FIG. 5A shows the results in a chart form, and FIG. 5B shows summarizing these results. Compound 1 (70% pure) hypoglycemic effects were tested in normal mice. Control group was orally fed 10% Tween 20. 40 mg/kg Group, 60 mg/kg Group, and 80 mg/kg Group are experimental groups fed with 40 mg/kg, 60 mg/kg, and 80 mg/kg, respectively. X axis indicates the time interval for glucose testings, and the Y axis indicates the blood glucose concentrations, wherein $p<0.05$ indicates significant difference and is marked as *; $p<0.01$ indicates highly significant difference and is marked as ; and $p≤0.001$ indicates extremely significant difference and is marked as *. These results indicate that Compound 1 (70% pure) at 80 mg/kg has a very good hypoglycemic effects in normal mice, and the hyproglycemic effects reaches 71%.

DEFINITIONS

Figure 1:
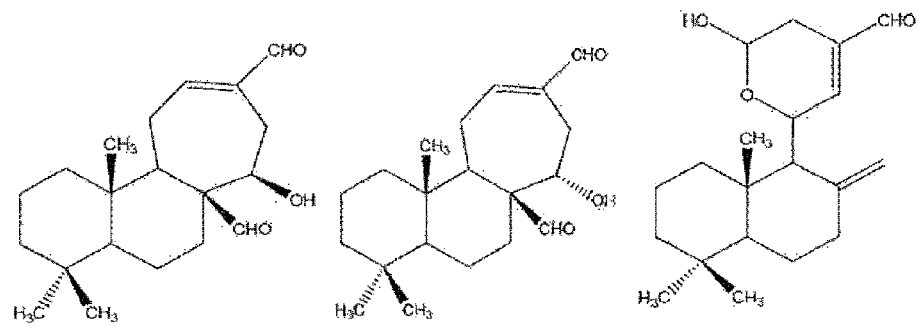
FIG. 1 shows compounds of galanal analogs isolated from ginger flower extracts.
Figure 1:
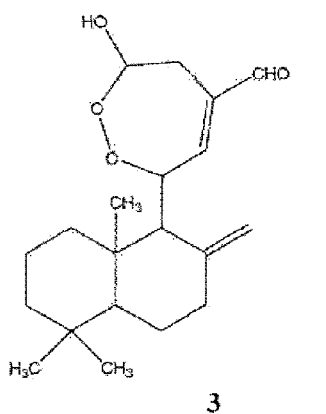
Figure 1:
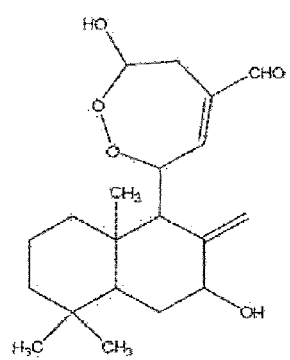
Figure 1:
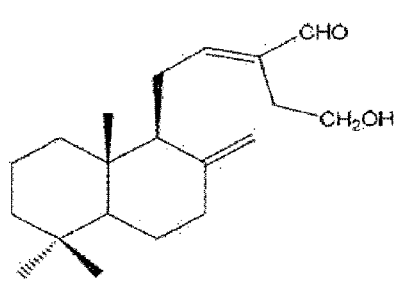
Figure 1:
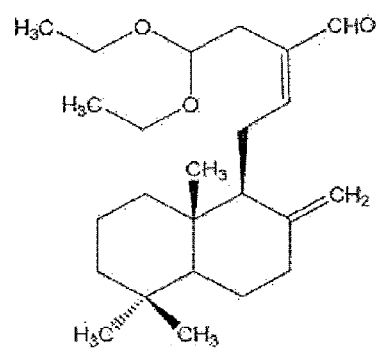

As used herein, the term "galanal analog" refers to diterpene analogs of Galanal B that have activities as GLP-1 potentiators. The term "galanal analog" includes the naturally occurring galanals, e.g., Galanal A and Galanal B. Examples of "galanal analogs" are shown as compounds 1-6, as well as compounds of general Formulae (A) and (B), in the following sections.

As used herein, the term "GLP-1 potentiator" refers to an agent that can potentiate the functions of GLP-1 or a GLP-1 analog. As noted in this description, GLP-1 exerts its functions by specific binding to the GLP-1 receptor, triggering specific signaling pathways that lead to biological functions including synthesis and release of insulin. Any agent that can potentiate such GLP-1 or GLP-1 analog functions is a "GLP-1 potentiator," regardless of its action mechanism.

As used herein, the term "glucagon-like peptide-1 receptor ligand" refers to any reagent that can activate the GLP-1 receptor (GLP-1R) to have similar functions as GLP-1. These ligands may be alternatively referred to as "GLP-1 analogs." That is, these two terms may be used interchangeably in this description. As used herein, the term "GLP-1 analogs" includes GLP-1 itself. Many GLP-1 analogs are known in the art, including GLP-1, exendin-4, exenatide, liraglutide, taspoglutide, albiglutide, and lixisenatide. Some of these are commercially available, clinically used, and marked under trade names. For example, Byetta® and Bydureon® are trade names of an exenatide compound marketed by Amylin Pharmaceuticals (San Diego, Calif.), and Victoza® is a trade name of liraglutide marked by Novo Nordisk (Denmark).

As used herein, the term "an effective amount" refers to an amount that can produce the desired biological effects or therapeutic outcomes. For example, for a GLP-1 potentiator, it refers to an amount that can produce a substantial potentiation of the effects resulting from GLP-1 binding to GLP-1R. Substantial potentiation refers to increase of about 10% or more, preferably about 20% or more, more preferably about 30% or more, and most preferably about 50% or more, as compared with a control in the absence of a potentiator. Finding such an effective amount involves only routine optimization procedures, and one skilled in the art would be able to determine such an amount without inventive efforts or undue experimentation.

As used herein, the term "alkyl" refers to a branched or unbranched hydrocarbon moiety. Preferably, the alkyl comprises 1 to 14 carbon atoms ($C_1$-$C_{14}$), more preferably 1 to 12 carbon atoms ($C_1$-$C_{12}$), 1 to 10 carbon atoms ($C_1$-$C_{10}$), 1 to 6 carbon atoms ($C_1$-$C_6$), or 1 to 4 carbon atoms ($C_1$-$C_4$). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it may be referred to as an alkenyl (double bond) or an alkynyl (triple bond) group. Furthermore, when an alkyl group is linked to an aryl group (defined below), it may be referred to as an "arylalkyl" group.

As used herein, the term "cycloalkyl" refers to an alkyl group as defined above that forms at least one ring. The cycloalkyl group preferably has 3-8 carbon atoms (e.g., $C_3$-$C_8$ cycloalkyl), preferably 4-7 carbon atoms (e.g., $C_4$-$C_7$ cycloalkyl), more preferably 5-7 carbon atom (e.g., $C_5$-$C_7$ cycloalkyl).

As used herein, the term "alkenyl" refers to a straight or branched hydrocarbon group having 2 to 20 carbon atoms ($C_2$-$C_{20}$) and containing at least one double bond. The alkenyl group preferably has 2-8 carbon atoms ($C_2$-$C_8$), more preferably 2-4 carbon atoms ($C_2$-$C_4$).

The term "aryl" refers to monocyclic or bicyclic aromatic hydrocarbon groups having 6-16 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, also refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

DETAILED DESCRIPTION

Embodiments of the invention related to GLP-1 potentiators and the use of these potentiators as therapeutics for blood glucose controls in diabetic patients. GLP-1 potentiators are agents that can potentiate the functions of GLP-1 or GLP-1 analogs. GLP-1 or a GLP-1 analog exerts its functions by binding to the GLP-1 receptor, triggering specific signaling pathways that lead to biological functions including synthesis and release of insulin. Any agent that can potentiate such GLP-1 or GLP-1 analog functions is a GLP-1 potentiator, regardless of its action mechanism.

Some embodiments of the invention relate to the use of galanal analogs as GLP-1 potentiators. These galanal analogs may be isolated from natural sources, such as from wild ginger flowers, or may be chemically synthesized. The chemically synthesized galanal analogs may be semisynthetic products, which may use a natural product as a starting material. Some embodiments of the invention relate to novel compounds that are derived from naturally occurring galanal analogs (e.g., Galanal B) by chemical modifications.

Embodiments of the invention relate to compounds for controlling blood glucose level that have structures shown in Formula I:

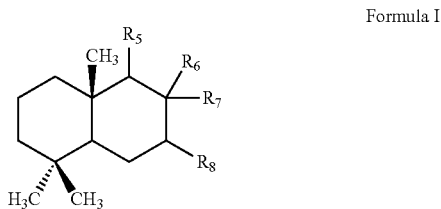

Formula I wherein $R_5$-$R_8$ are as defined above.

Some embodiments of the invention relate to methods for controlling blood glucose level includes administering to a subject in need thereof a compound of Formula I. The method further includes administering to the subject a GLP-1 receptor ligand. The compound and the GLP-1 receptor ligand may be administered together. The compound may be Galanal A or Galanal B. The GLP-1 receptor ligand may be GLP-1 or exendin-4.

As noted above, GLP-1 is a member of secretin family that can regulate blood glucose levels. GLP-1 is derived from proglucagon. Secretion of GLP-1 by ileal L cells depends on the presence of nutrients in the lumen of the small intestine. The potent anti-hyperglycemic effects of GLP-1 include glucose-dependent stimulation of insulin secretion, while suppressing glucagon secretion. Such glucose-dependency is very attractive because GLP-1 would not stimulate insulin release to cause hypoglycemia (over reduction of blood glucose) when the plasma glucose concentration is in the normal fasting range.

GLP-1 binds specifically to GLP-1 receptor, which is a G-protein-coupled receptor (GPCR) with seven transmembrane domains. Binding of GLP-1 to GLP-1 receptors (GLP-1R) stimulates the adenylate cyclase pathway, which eventually leads to increased insulin synthesis and release. Therefore, GLP-1R has been suggested as a potential target for diabetes treatments.

Embodiments of the present invention are based on the use GLP-1R as a target to develop new hypoglycemic drugs. Based on this approach, inventors of the present invention have found that wild ginger flower extracts contain molecules that can potentiate the GLP-1/GLP-1R mediated biological actions. These molecules are referred to as "GLP-1 potentiators" in this description.

Gingers have been widely used as spice and food ingredients. Gingers contain diterpenes, such as Galanal A, Galanal B. These terpenoids have been found to have various biological activities, including antimicrobial effects (Abe et al., "*Antimicrobial Activities of Diterpene Dialdehydes, Constituents from Myoga (Zingiber mioga Roscoe), and Their Quantitative Analysis*," Bioscie. Biotechnol. Biochem., 68 (7), 1601-1604 (2004)). In addition, galanals A and B have been found to have antitumor effects (Miyoshi et al., "*Dietary ginger constituents, galanals A and B, are potent apoptosis inducers in Human T lymphoma Jurkat cells*," Cancer Lett., 199 (2), 113-9 (2003)). However, there is no report that gingers are beneficial in blood glucose controls for diabetic patients.

Inventors of the present invention have unexpected found that wild ginger flower extracts contain active ingredients that can potentiate the effects of GLP-1. Specifically, diterpenoids such as Galanal A, Galanal B and analogs, which are generally referred to as "galanal analogs" in this description, in the ginger flower extracts have been found to be able to potentiate the biological functions mediated by the specific binding of GLP-1 to its receptor.

The extracts may be alcohol or organic solvent extracts. Suitable solvents for such extractions, for example, may include alcohols (e.g., methanol, ethanol, or propanol), esters (e.g., ethyl acetate), alkanes (e.g., hexane), or haloalkanes (e.g., chlronethane or chloroethane). In preferred embodiments, the extracts are alcohol extracts. Such extracts may be used as is, or they may be dried and sued as dried extracts.

Furthermore, the active ingredients in the wild ginger flower extracts may be purified and characterized. Specifically, the following compounds 1-6 have been isolated from wild ginger flower extracts and have been characterized to have the structures shown below:

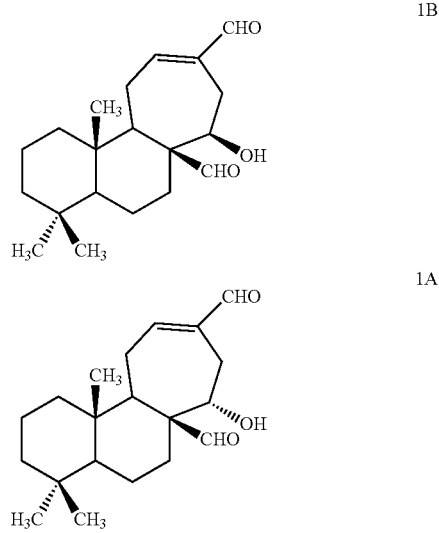

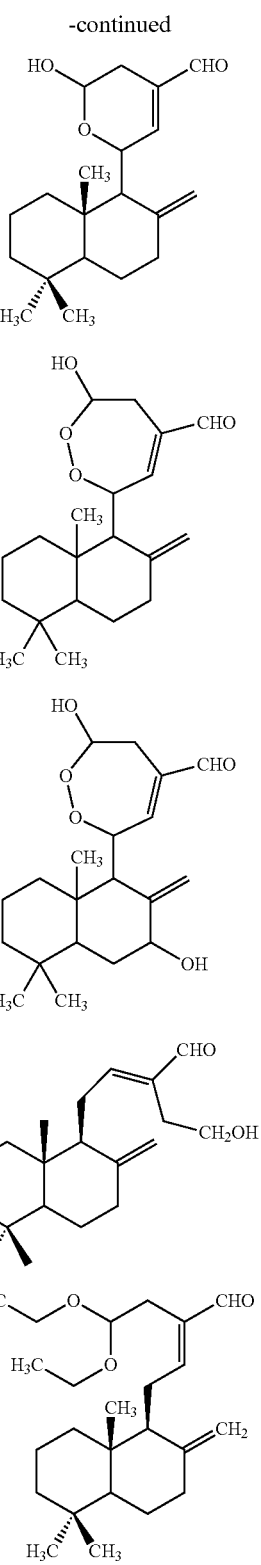

Wherein compound 1A is Galanal A, compound 1B is Galanal B; compound 2 is 11-hydroxy-8(17),12(E)-labda-dien-15,16-dial 11,15-hemiacetal; compound 3 is Coronarin B, compound 4 is 7β-Hydroxycoronarin B; compound 5 is (E)-labda-8(17),12-diene-15-ol-16-al; and compound 6 is (E)-15,15-diethoxylabda-8(17),12-dien-16-al.

Figure 4:
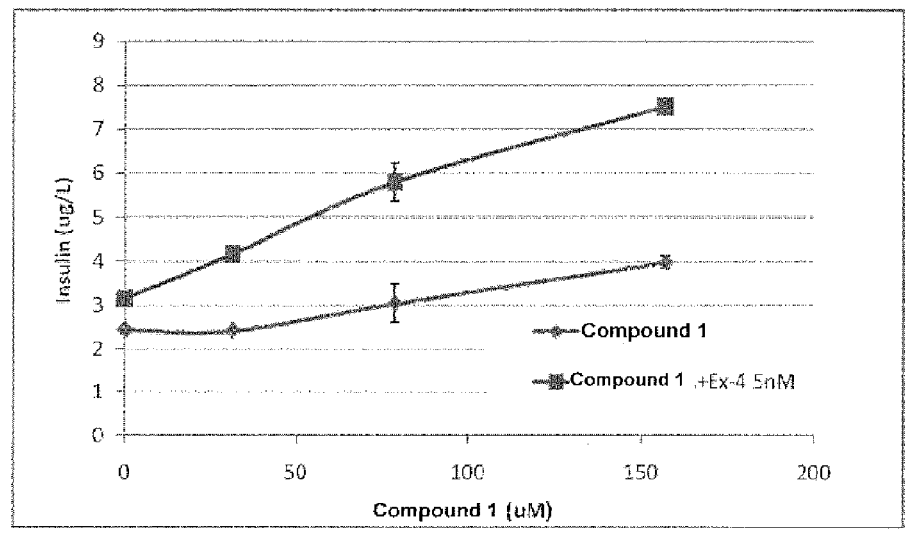
FIG. 4 shows the GLP-1 potentiator effects of compounds 1, 2, and 3 in accordance with embodiments of the invention.
Figure 4:
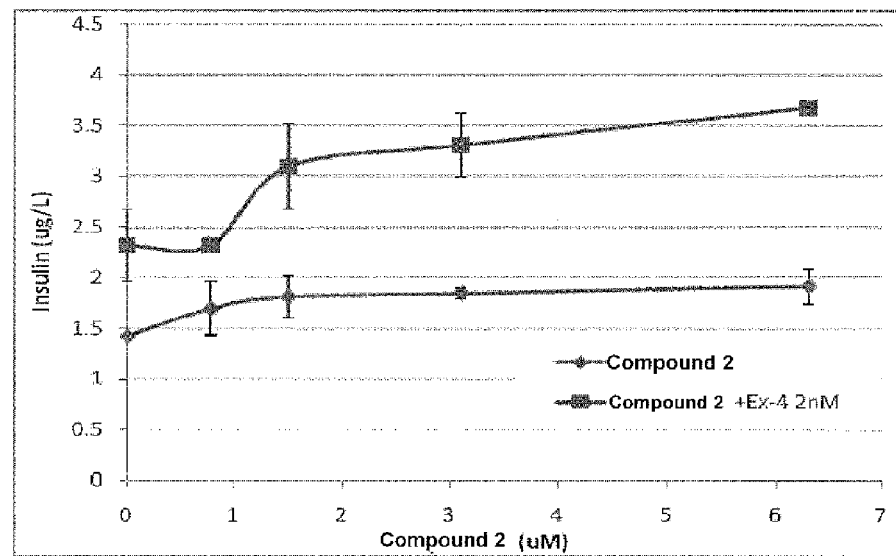
Figure 4:
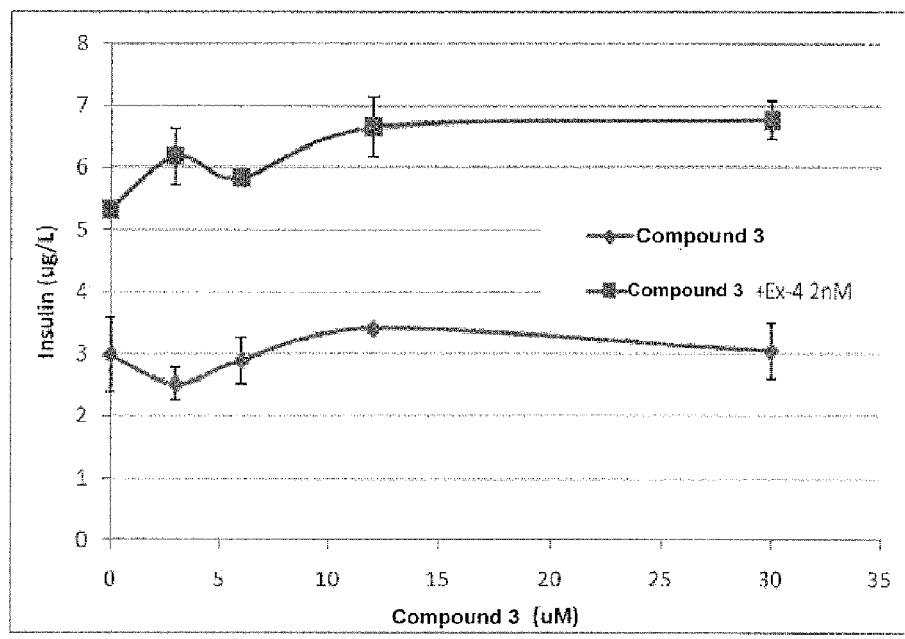

The diterpenoid compounds of the invention may be developed as GLP-1 receptor positive regulators that can be used to potentiate (enhance) the responses of GLP-1/GLP-1R interactions. As shown in FIG. 4, these compounds are effective potentiators of GLP-1 analogs (e.g., exendin-4). Specifically, in the examples shown in FIG. 4, compounds 1, 2, and 3 can enhance the function of exendin-4 leading to enhanced release of insulin.

Thus, compounds of the invention can be used to potentiate the effects of GLP-1 in increasing insulin secretion and lowering blood glucoses. Accordingly, they can be used to prepare anti-diabetic therapeutic agents for use with GLP-1 or GLP-1 analogs. In accordance with embodiments of the invention, these GLP-1 potentiators can be used together with any ligand of the GLP-1 receptor. Ligands of the GLP-1 receptor will include GLP-1 and other GLP-1 analogs, such as exendin-4, exenatide, liraglutide, taspoglutide, albiglutide, and lixisenatide. Some of these GLP-1 analogs are commercially available, clinically used, and may be marketed under trade names. For example, Byetta® and Bydureon® are trade names of an exenatide compound marketed by Amylin Pharmaceuticals (San Diego, Calif.), and Victoza® is a trade name of liraglutide marked by Novo Nordisk (Denmark).

Some embodiments of the present invention relates to applications of the above mentioned compounds to lower blood glucose levels, to increase insulin levels, to reduce insulin resistance, and to treat and/or prevent diabetes. Because these compounds are GLP-1 potentiators, they enhance the functions of GLP-1 and analogs. GLP-1 functions have been found to be glucose-dependent and, therefore, GLP-1 and its analogs have little risk of lowering fasting blood glucose. Therefore, the effects of compounds of the present invention are also glucose-dependent. These compounds are different from the traditional sulfonylurea compounds, and they will not reduce fasting blood glucose levels in individuals and they would have fewer side effects.

A method in accordance with embodiments of the invention for controlling blood glucose levels may comprise administering an effective amount of a compound of the invention (e.g., a galanal analog) to a subject in need thereof together with a GLP-1 analog.

In addition to the above described compounds (i.e., galanal analogs) that are isolated from ginger flower extracts, some embodiments of the invention relate to novel compounds that are chemically synthesized. These compounds may be semi-synthetic compounds that are chemically modified from the naturally occurring compounds, such as Galanal B. These chemically synthesized compounds are also GLP-1 potentiators.

Figure 2:
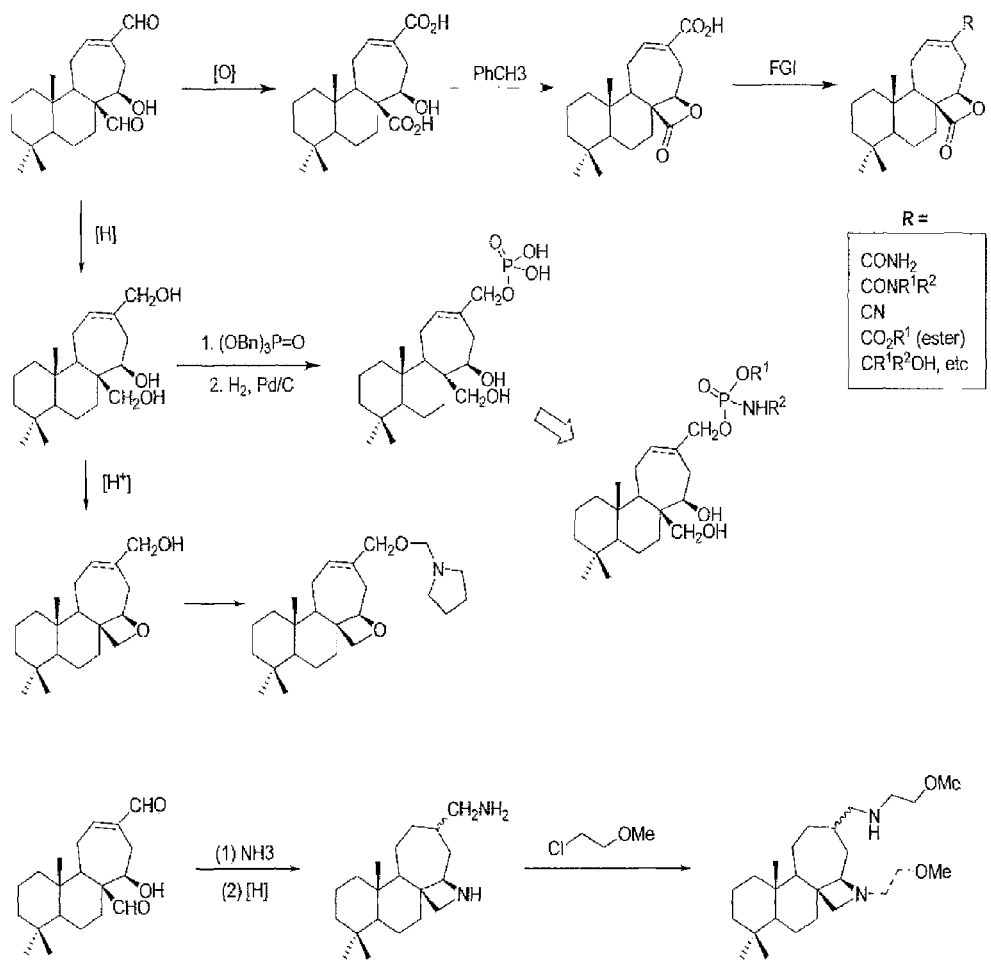
FIG. 2 shows reaction schemes for semisynthesis of compounds of the invention using Galanal B as a starting material.

For example, one can start from compound 1 (Galanal B) to design and synthesize new GLP-1 receptor positive regulators. FIG. 2 illustrates examples of the synthetic procedures for synthesizing some of the modified compounds. Embodiments of the invention also relate to these new therapeutic compounds and their use in controlling blood glucose levels.

These new compounds may be derived from Galanal B via synthetic modifications. These compounds may be represented with the general Formulae (A) and (B). As shown in FIG. 2, compounds of Formula (A) and Formula (B) may be synthesized by common chemical reactions using Galanal B as a starting material.

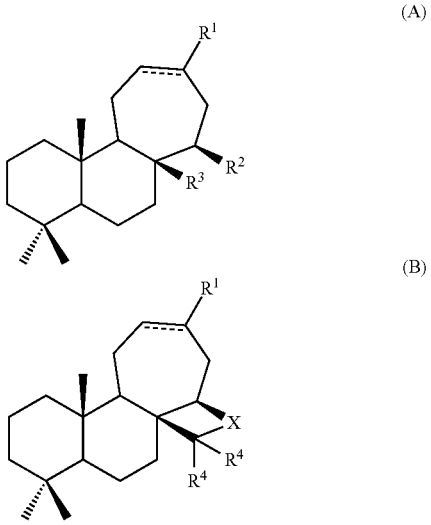

wherein R[1] is —CONR'R", —CN, —CO$_2$R', or —CR'R"OH; R[2] is —OR' or —NR'R"; R[3] is —CHO, —CH$_2$OR', or —CO$_2$R'; R[4] are both —H or together form =O; X is —O— or NR', wherein R' and R" are independently selected from H, alkyl, alkenyl, cycloalkyl, or aryl.

Embodiments of the invention will be further illustrated with the following examples. These examples are provided for illustration only and are not intended to limit the scope of the invention. One skilled in the art would appreciate that variations and modifications are possible without departing from the scope of the invention.

EXAMPLES

Example 1

Purification and Characterization of Galanal B and Analogs

Materials and Methods

General Procedures.

Optical rotations are recorded on a JASCO-370 polarimeter using an appropriate solvent. UV spectra are obtained in MeOH on a JASCO model 7800 UV-Vis spectrophotometer. IR spectra are measured on a Hitachi 260-30 spectrophotometer. $^1$H (400 MHz) and $^{13}$C NMR (100 MHz) spectra and $^1$H-$^1$H COSY, NOESY, HMQC, and HMBC experiments are recorded on a Varian Unity-400NMR spectrometer. MS measurements are obtained on a JMS-HX100 mass spectrometer. Silica gel (Merck), particle size 15-40 μM, is used for column chromatography. Silica gel 60 F254 precoated aluminum sheets (0.2 mm, Merck) are employed for TLC. All solvents are of HPLC grade.

Plant Material.

The leaves and pseudostem of *Hedychium coronarium* Koenig are collected at Ping-Tung Hsien, Taiwan, in August 2009. Fresh *H. coronarium* is dried under a stream of heated air at 60° C. for 5 to 8 hr.

Extraction and Isolation.

The dried materials are chopped and ground to suitable particle sizes (e.g., 20 mesh) prior to extraction with an appropriate solvent (e.g., 10 litter of ethanol for every kilogram of dried plant). The ethanol extracts of the active plants are partition with distilled water (dH$_2$O), ethyl acetate, butanol, and hexane. Recovery weight and activity from each fraction are measured, and the specific activity and total activity will be calculated.

[Method 1] The ethanol extracts of the active plant ingredients (16.9 g) are partition with dH$_2$O, ethyl acetate, butanol, and hexane. The hexane fraction is concentrated under reduced pressure to afford a brown residue (6.47 g). The residue is fractionated by chromatography over silica gel and resolved into 10 fractions. The activities are recovered in fraction E-2-L. Fraction E-2-L is subjected to repeated chromatography on silica gel and eluted with hexane-EtOAc (7:3) to yield compound 1 (5 mg).

[Method 2] The ethanol extracts of the active plant ingredients (72.58 g) are partition with 90% EtOH/H$_2$O and hexane. The 90% EtOH/H$_2$O fraction is partition with ethyl acetate and dH$_2$O. The resultant ethyl acetate fraction is dried (9.71 g) and chromatographed over a silica gel column and eluted with n-hexane containing increasing amounts of EtOAc, followed with a final wash using MeOH to yield 13 fractions. Fraction 2 is further purified on a silica gel column and eluted with hexane-EtOAc (8:2) to yield compound 2 (8 mg). Fraction 3 is further purified on a silica gel column eluted with hexane-EtOAc (7:3) to yield compound 5 (18 mg) and compound 6 (35 mg). The ethyl acetate fraction containing most of the activities is subjected to repeated chromatography on silica gel. The column is usually washed with a non-polar solvent such as hexane, then eluted by steps of increasing polarity by mixing increasing amounts of ethyl acetate in hexane (5, 10, 20, 30, 40, 50, 75 and 100%), followed by eluting with 20% and 50% of methanol in ethyl acetate. The active fraction is subjected to repeated chromatography on RP18 and eluted with ACN-H$_2$O (7:3) to yield compound 3 (15 mg). Fractions of a fixed volume are collected and subjected to receptor internalization assay. Specificity is obtained and total activity yield is calculated.

Results

Identification of Compounds 1, 2, 3, 4, 5 and 6:

Galanal B (Compound 1):

Colorless needles, mp 134-136° C.; UV$_{max}$λ (EtOH) nm (ε) 236 (8900); IR$_{max}$ν(CHCl$_3$ on NaCl) cm$^{-1}$:3610 (OH), 1711 (C=O), 1680 (C=O), 1646 (C=C); $^1$HNMR (CDCl$_3$) δ: 0.81 (3H, s, H-18), 0.79 (3H, s, H-20), 0.90 (3H, s, H-19), 1.52 (1H, d, J=10.0 Hz, H-9), 2.58 (1H, m, H-11), 2.70 (1H, m, H-14), 2.94 (1H, m, H-14), 3.15 (1H, m, H-11), 3.57 (1H, dd, J=1.8, 9.0 Hz, H-15), 7.06 (1H, dd, J=4.5, 8.5 Hz, H-12), 9.43 (1H, s, H-16), 10.43 (1H, s, H-17); $^{13}$C NMR (CDCl$_3$) δ: 38.8 (C-1), 18.9 (C-2), 41.6 (C-3), 33.3 (C-4), 55.5 (C-5), 18.5 (C-6), 34.4 (C-7), 55.3 (C-8), 55.4 (C-9), 38.9 (C-10), 24.1 (C-11), 157.6 (C-12), 140.7 (C-13), 28.7 (C-14), 78.7 (C-15), 193.4 (C-16), 208.1 (C-17), 33.2 (C-18), 21.3 (C-19), 16.6 (C-20); ESI-MS m/z: 341 (M+Na).

11-hydroxy-8(17),12(E)-labdadien-15,-16-dial 11,15-hemiacetal (compound 2)

colorless gum-like substance; [α]$^{25}_D$–40.0° (c 0.43, CHCl$_3$); UV$_{max}$λ (MeOH) nm (log ε) 233.5 nm (4.13); IR$_{max}$ν (KBr) cm$^{-1}$: 3396 (—OH), 2933, 2873, 2842, 1682 (conjugated —CHO), 1645, 1643, 1462, 1442 1214, 1167, 1083, 1049, 898, 667; $^1$HNMR (CDCl$_3$) δ: 0.83 (3H, s, H-18), 0.87 (3H, s, H-19), 0.97 (3H, s, H-20), 1.09 (1H, dd, J=2.9, 12.7 Hz, H-5), 2.20 (1H, br d, J=2.6 Hz, H-9), 2.69 (1H, dd, J=8.6, 15.6 Hz, H-14), 3.33 (1H, dd, J=5.3, 15.6 Hz, H-14), 4.79 (1H, br s, H-17), 4.83 (1H, br s, H-17), 5.45 (1H, dd, J=5.3, 8.6 Hz, H-15), 5.52 (1H, dd, J=2.6, 2.6 Hz, H-11), 6.45 (1H, t, J=2.6 Hz, H-12), 9.39 (1H, s, H-16); $^{13}$C NMR (CDCl$_3$) δ: 39.1 (C-1), 19.2 (C-2), 42.0 (C-3), 33.7 (C-4), 55.9 (C-5), 23.9 (C-6), 37.9 (C-7), 144.9 (C-8), 62.2 (C-9), 40.1 (C-10), 85.8 (C-11), 155.9 (C-12), 136.4 (C-13), 28.0 (C-14), 101.9 (C-15), 192.5 (C-16), 109.2 (C-17), 33.5 (C-18), 21.6 (C-19), 16.7 (C-20); ESI-MS m/z: 341 (M+Na).

Coronarin B (Compound 3):

Colorless oil, mp 134-136° C.; [α]$^{25}_D$–43.1° (c 0.14, CHCl$_3$); UV$_{max}$λ (EtOH) nm (ε) 235(7800), 205 (4700); IR$_{max}$ν (KBr) cm$^{-1}$: 3620 (—OH), 3090, 1650, 895 (exomethylene bands), 1780, 1755 (C=O); $^1$HNMR (CDCl$_3$) δ:

0.84 (3H, s, H-18), 0.88 (3H, s, H-19), 0.98 (3H, s, H-20), 2.20 (1H, dd, J=1.2, 2.5 Hz, H-9), 2.68 (1H, m, H-14), 3.33 (1H, dd, J=5.4, 15.5 Hz, H-14), 4.80 (1H, d, J=1.2 Hz, H-17), 4.84 (1H, s, H-17), 5.48 (1H, ddd, J=5.4, 5.6, 8.5 Hz, H-15), 5.55 (1H, ddd, J=2.3, 2.5, 4.1 Hz, H-11), 6.44 (1H, s, H-12), 9.40 (1H, s, H-16); $^{13}$C NMR (CDCl$_3$) δ: 39.1 (C-1), 19.2 (C-2), 42.1 (C-3), 33.6 (C-4), 55.9 (C-5), 24.0 (C-6), 38.0 (C-7), 145.0 (C-8), 62.2 (C-9), 40.2 (C-10), 85.8 (C-11), 155.9 (C-12), 136.5 (C-13), 28.1 (C-14), 101.9 (C-15), 192.4 (C-16), 109.2 (C-17), 33.7 (C-18), 21.6 (C-19), 16.7 (C-20); ESI-MS m/z: 341 (M+Na).

7β-Hydroxycoronarin B (Compound 4)

Oil; $[α]^{25}_D$ −26.5° (c 0.79, CHCl$_3$); IR$_{max}$ν (KBr) cm$^{-1}$: 3580, 3020, 1684, 1650, 950; $^1$HNMR (CDCl$_3$) δ: 0.84 (3H, s, H-18), 0.97 (3H, s, H-19), 0.91 (3H, s, H-20), 2.06 (1H, d, J=3 Hz, H-9), 2.74 (1H, m, H-14), 3.35 (1H, dd, J=16.6 Hz, H-14), 3.98 (1H, dd, J=12, 6 Hz, H-7), 4.80 (1H, d, J=1.2 Hz, H-17), 4.84 (1H, s, H-17), 5.49 (1H, dd, J=5, 9 Hz, H-15), 5.55 (11, ddd, J=4, 3, 2 Hz, H-11), 6.40 (1H, s, H-12), 9.38 (1H, s, H-16); $^{13}$C NMR (CDCl$_3$) δ: 39.1 (C-1), 19.2 (C-2), 41.8 (C-3), 33.7 (C-4), 53.6 (C-5), 33.5 (C-6), 73.5 (C-7), 146.7 (C-8), 60.2 (C-9), 39.8 (C-10), 85.6 (C-11), 155.1 (C-12), 136.8 (C-13), 28.1 (C-14), 102.0 (C-15), 192.3 (C-16), 106.1 (C-17), 33.8 (C-18), 21.5 (C-19), 16.7 (C-20); ESI-MS m/z: 357 (M+Na).

(E)-labda-8(17),12-diene-15-ol-16-al (compound 5)

white, amorphous solid; $[α]^{25}_D$ +15.5° (c 0.15, CHCl3); IR (film) îmax 3430, 3100, 2929, 1685, 1639, 1460, 1023, 889 cm−1; $^1$HNMR (CDCl$_3$) δ: 0.83 (3H, s, H-18), 0.89 (3H, s, H-19), 0.97 (3H, s, H-20), 1.16 (1H, dd, J=13, 3 Hz, H-5), 1.91 (brd, H-9), 2.47 (1H, ddd, J=17, 11, 7 Hz, H-11), 2.60 (2H, H-14), 2.64 (1H, ddd, J=17, 6, 3 Hz, H-11), 3.68 (2H, H-15), 4.40 (1H, brd, H-17), 4.86 (1H, brd, H-17), 6.58 (1H, dd, J=7, 6 Hz, H-12), 9.35 (1H, s, H-16); $^{13}$C NMR (CDCl$_3$) δ: 39.2 (C-1), 19.3 (C-2), 41.9 (C-3), 33.5 (C-4), 55.4 (C-5), 24.3 (C-6), 37.8 (C-7), 148.1 (C-8), 56.5 (C-9), 40.1 (C-10), 24.1 (C-11), 159.3 (C-12), 140.1 (C-13), 28.1 (C-14), 61.3 (C-15), 195.9 (C-16), 107.8 (C-17), 33.5 (C-18), 21.7 (C-19), 16.7 (C-20); ESI-MS m/z: 327 (M+Na).

(E)-15,15-diethoxylabda-8(17),12-dien-16-al (compound 6)

amorphous oil; $[α]^{25}_D$+13° (c 0.2, CHCl3); $^1$HNMR (CDCl$_3$) δ: 0.74 (3H, s, H-20), 0.82 (3H, s, H-18), 0.89 (3H, s, H-19), 1.16 (6H, t, J=6.9 Hz, ethoxy CH3), 1.89 (1H, brd, J=9.9 Hz, H-9), 2.53 (1H, m, H-11A), 2.58 (2H, m, H-14), 2.63 (1H, dm, H-11B), 3.48 and 3.76 (each 2H, m, ethoxy CH2), 4.41 (1H, d, J=1.2 Hz, H-17), 4.53 (1H, t, J=5.4 Hz, H-15), 4.82 (1H, d, J=1.2 Hz, H-17), 6.54 (1H, t, J=6.2 Hz, H-12), 9.33 (1H, s, H-16); $^{13}$C NMR (CDCl$_3$) δ: 39.1 (C-1), 19.1 (C-2), 41.1 (C-3), 33.4 (C-4), 55.3 (C-5), 24.0 (C-6), 37.7 (C-7), 148.3 (C-8), 56.4 (C-9), 39.4 (C-10), 24.5 (C-11), 160.3 (C-12), 138.4 (C-13), 30.1 (C-14), 102.1 (C-15), 195.2 (C-16), 108.1 (C-17), 33.4 (C-18), 21.5 (C-19), 14.2 (C-20), 62.7 (C-1'), 62.8 (C-1''), 15.1 (C-2'), 15.2 (C-2''); ESI-MS m/z: 399 (M+Na).

Example 2

Semi-Synthesis of GLP-1 Potentiators

Semi-Synthesis of GLP-1 Potentiators example

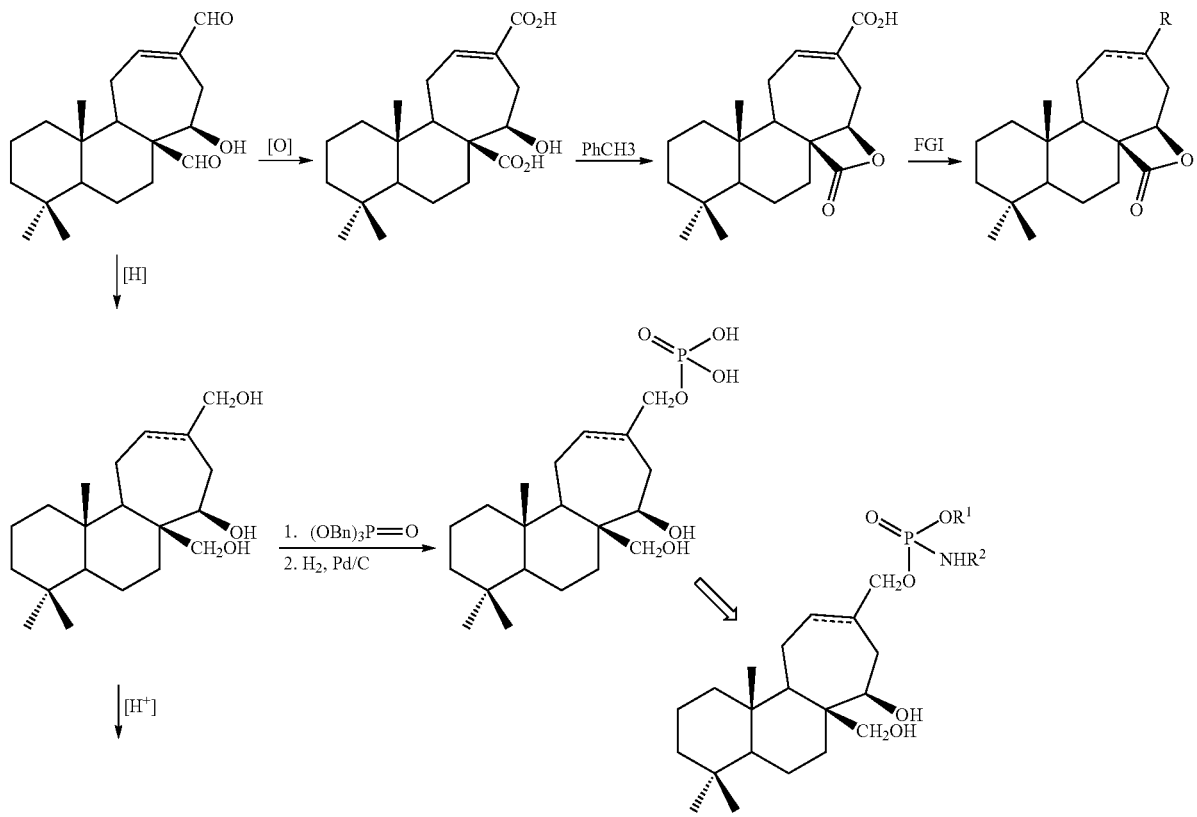

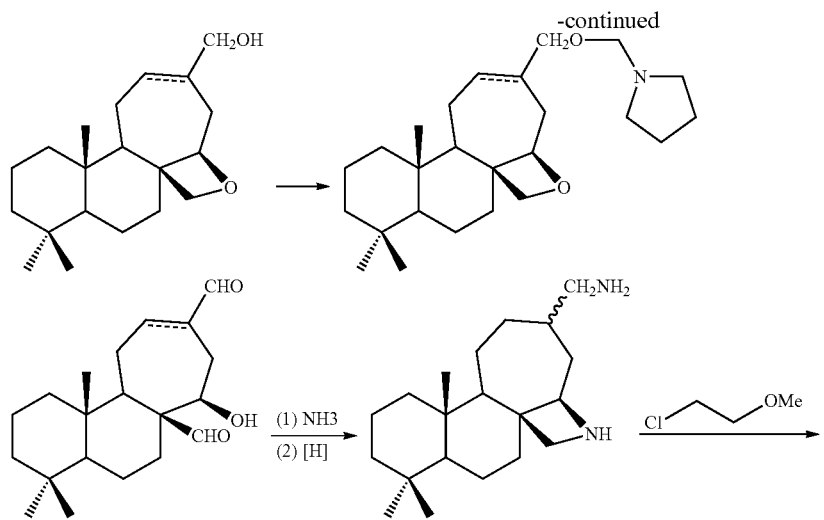

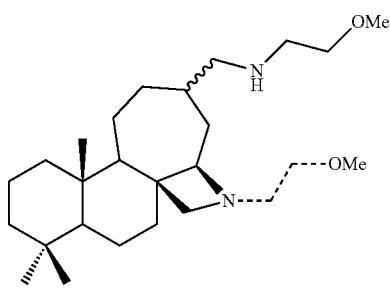

R = CONH$_2$
CONR$^1$R$^2$
CN
CO$_2$R$^1$ (ester)
CR$^1$R$^2$OH, etc

Example 3

Receptor Arrestin Translocation Assay

Experimental Design:

In U2OS cells (Human Bone Osteosarcoma, available from Sigma-Aldrich) transfected with GLP-1 receptor gene, the GLP-1 receptors are highly expressed on the cell membrane. After activation, the cell surface GLP-1 receptors will undergo endocytosis, which can be used as quantitative assays for physiological (active) cells. For example, these cells may be plated as monolayer on a test plate (e.g., a 384-well plate). The cells, for example, may be plated at a density of 4000 cells per well. The test sample concentrations may be 0.2-0.000002 mg/ml. The test volumes may be 25 microliter, and the test time may be 1 hr.

GLP-1 receptors are G-protein coupled receptors with seven transmembrane domains. After activation by hormones or neural stimulants, many G-protein coupled cell surface receptors will internalize from the cell surface to the cytoplasm in endocytosis responses. Thus, the GLP-1 receptors on the U2OS cell surface will undergo endocytosis after activation by the test samples. This process may be used to assay the test samples. The extents of receptor endocytosis are closely related to the concentrations of the test samples—the higher the sample concentrations, the stronger the endocytosis responses. Because the densities of cell surface receptors are fixed, when the sample concentrations reach a high number, the extents of endocytosis responses would not increase with increasing sample concentrations, i.e., the response reaches saturation. Based on the concentrations and saturation measurements, one can determine the receptor binding affinities of the test samples.

After activation of G-protein coupled receptors, the receptors are typically desensitized or inactivated. Arrestin is involved in such desensitization or inactivation processes. That is, arrestin will be recruited to the GPCR to desensitize or inactivate the receptors. Therefore, monitoring the translocation of GFP-tagged arrestin from the cytosol to the activated GPCRs on the plasma membrane would allow one to measure the binding of test compounds to the receptor target. (Hudson et al., "*High-content screening of know G protein-coupled receptors by arrestin translocation*," Methods Enzymol., 414: 63-78 (2006)).

Figure 3:
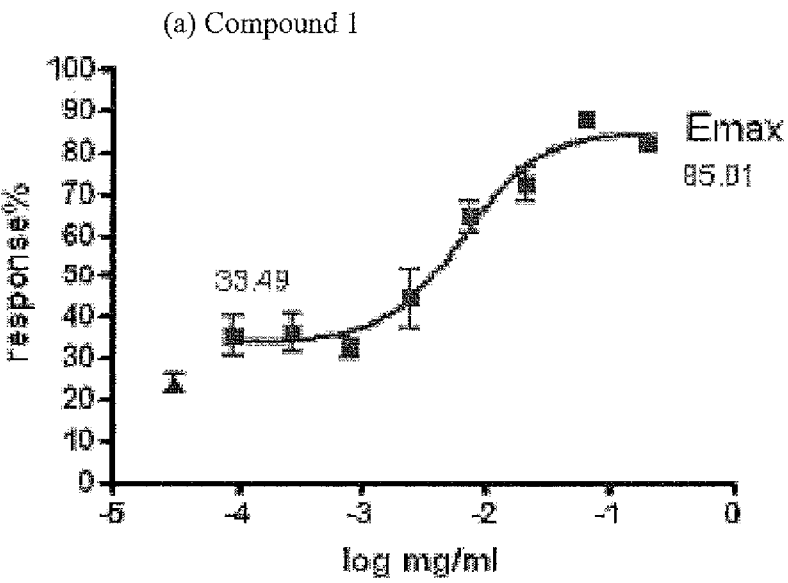
FIG. 3 shows effects of compounds of the invention and their $EC_{50}$ values.
Figure 3:
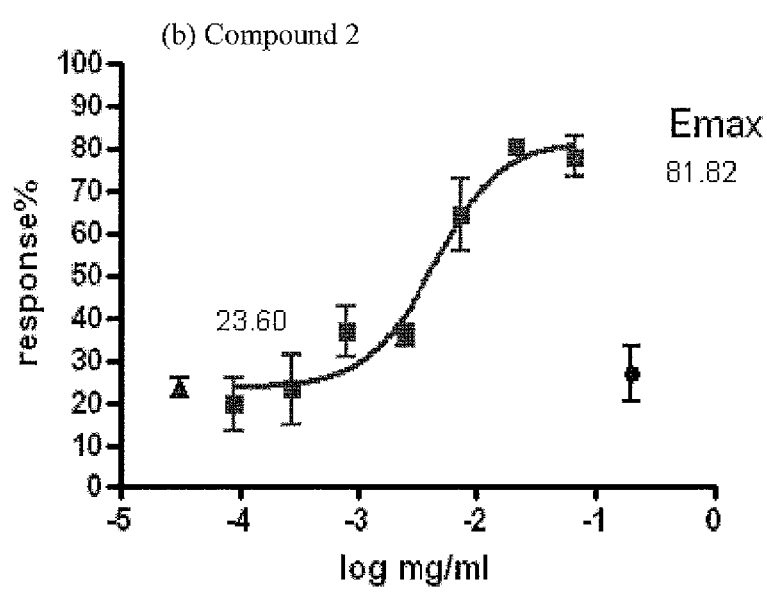
Figure 3:
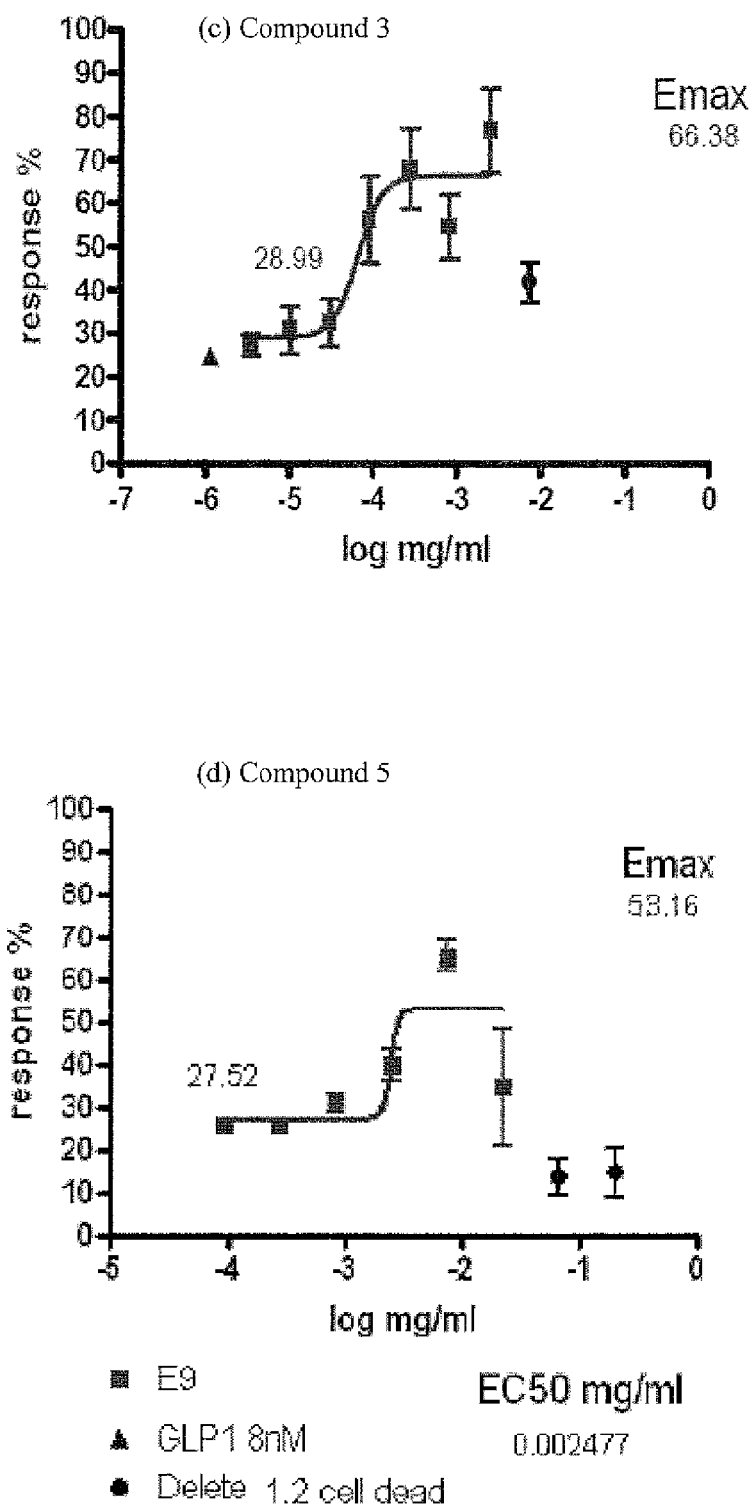
Figure 3:
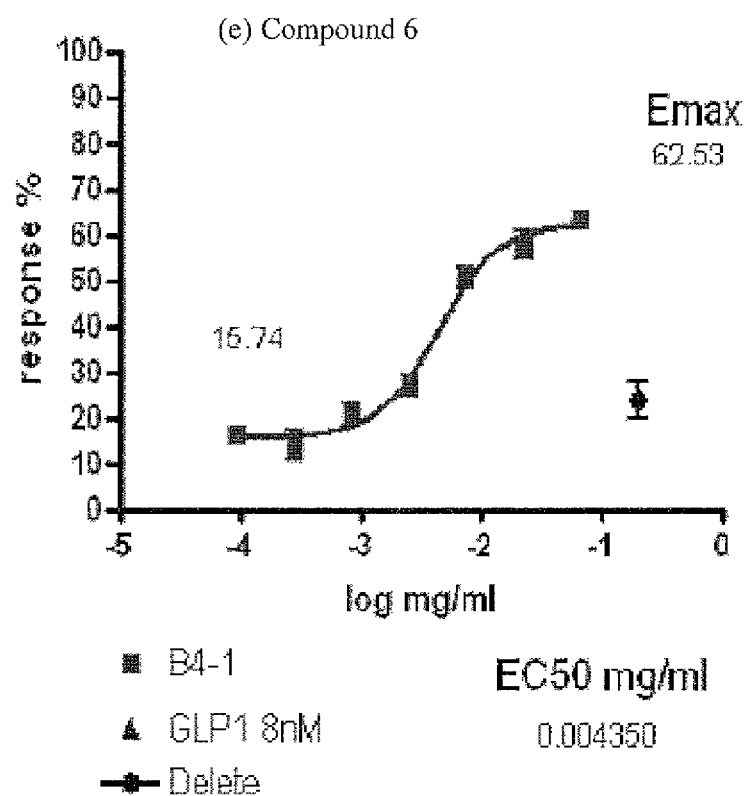

Therefore, using receptor arrestin translocation assay, the binding of GLP-1 to GLP-1R can be monitored. Furthermore, this assay can be adapted to monitor GLP-1 potentiator activities—e.g., by keeping the concentrations of GLP-1 and GLP-1R constant and varying the concentrations of the potentiators to be tested. Using this assay, the following test samples have been assessed: (a) compound 1 (MW 318), (b) compound 2 (MW 318), (c) compound 3 (MW 334), (d) compound 5 (MW 304), (e) compound 6 (MW 376). In these assays, the concentration of GLP-1 is 4-8 nM, and the concentrations for the test samples range from 0.001 mg/ml to 1 mg/ml. Upon activation by GLP-1, in the presence of the test samples (GLP-1 potentiators), the GLP-1/GLP-1 receptor complexes on the U2OS cell surface will undergo endocytosis; higher test sample concentrations would elicit stronger GLP-1/GLP-1R responses—hence, stronger endocytosis responses. When the sample concentrations reach certain high concentrations, the extents of endocytosis responses will not further increase with increasing sample concentrations because the responses have reached saturation. FIG. 3 shows results of such assays.

Based on the binding curves and saturation measurements as a function of test sample concentrations, the receptor affinities of the test samples can be determined. Based on the results shown in FIG. 3, the affinities of the test compounds are as follows: (a) compound 1, $EC_{50}$=6.603 μg/ml; (b) compound 2, $EC_{50}$=4.438 μg/ml; (c) compound 3, $EC_{50}$=0.06569 μg/ml; (d) compound 5, $EC_{50}$=2.477 μg/ml; and (e) compound 6, $EC_{50}$=4.350 μg/ml.

These results show that this series of diterpenoids achieve their blood glucose lowering effects via regulatory mechanisms that are mediated by GLP-1/GLP-1R signaling. These results also show that all these test compounds are powerful potentiators of GLP-1, with compound 3 being the most potent.

Experiment 4

Insulin Secretion Tests in Rat Pancreatic Beta Cells RINm5F

Cell culture

Rat pancreatic beta cell line RINm5F was purchased from the Food Industry Research and Development Institute (Hsinchu, Taiwan), No. BCRC 60410; source: ATCC CRL-11 605. The cells are cultured in 10% FBS RPMI-1640 medium, in a constant temperature $CO_2$ incubator, under 5% $CO_2$, 37° C. and 95% humidity, for subsequent experiments.

Operation Steps

To each 96-well plate, add the RINm5F cells ($8 \times 10^5$ cells/well) and culture the cells for 2 days before the experiments. Before testing, remove the culture medium. To each well in the 96-well plates, add 100 ul of KRPH buffer (136 mM NaCl, 4.8 mM KCl, 1.2 mM $CaCl_2$, 1.2 mM $KH_2PO_4$, 1.2 mM $MgSO_4$, 5 mM $NaHCO_3$, 10 mM HEPES), 2.8 mM D-glucose, 0.2% bovine serum albumin, pH 7.4, placed in a $CO_2$ incubator at 37° C. for 30 minutes, to allow the pancreatic islet cells to acclimate to the medium change (from RPMI 1640 to KRPH buffer). Remove the 96-well plates from the incubator. After removing the culture medium, rinse the cells with KRPH buffer +0.2% BSA, add different concentrations of test samples, as well as a GLP-1 analog (Exendin-4). Incubate the cells in KRPH buffer and glucose (KRPH +0.2% BSA, 16 mM glucose) containing culture medium for 2 hours to allow for insulin secretion by the islet beta cells under glucose stimulation. The supernatants from the incubation are collected and the concentrations of insulin released in the wells are assayed using ELISA. Various insulin ELISA kits are available from commercial sources, such as Calbiotech (Spring Valley, Calif.), Crystal Chem., Inc. (Downers Grove, Ill.), and Mercodia (Uppsala, Sweden).

Experimental Results

Two days after inoculating RINm5F cells, about $8 \times 10^5$ cells/well in 96-well plates, add the active ingredients, compounds 1, 2, and 3, from wild ginger flower 95% ethanol extracts, to the cells. Exendin-4 (2 nM for compound 1 or 5 nM for compounds 2 and 3) is added as a substitute for GLP-1. After 2 hours, the insulin contents in the supernatants are assessed using insulin ELISA kits.

As shown in FIG. 4, compounds 1, 2, and 3 stimulate more insulin secretions when exendin-4 is added. However, when these compounds are used in the absence of exendin-4, they effect is substantially abolished. These results suggest that stimulation of insulin secretions by compounds 1, 2, and 3 is mediated by exendin-4/GLP-1R binding. These results are consistent with the notion that these compounds are potentiators of GLP-1 (and exendin-4), and they are not themselves effective GLP-1R ligands for inducing hypoglycemic effects.

Example 5

Compounds 1 (Purity 70%) in Normal Mice Intraperitoneal Glucose Tolerance Test (IPGTT)

In this example, in vivo IPGTT is used to validate the blood glucose lowering activity of compound 1 (purity 70%). Twenty-four (24) six weeks old C57BL/6J mice are fed normal diets in an environment of 12/12 light-dark cycles and a constant temperature controlled at 24±2° C. with an unlimited supply of water and food. The mice are divided into four groups of six each, including a control group and three compound 1 (purity 70%) groups. The three compound 1 groups are respectively given orally compound 1 at dosages of 40 mg/Kg, 60 mg/Kg, and 80 mg/Kg. Mice fasted overnight are allowed to eat for 1 hour. After feeding, wait for another hour before giving the test drugs. Thirty (30) minutes after drug administration, glucose at a dose of 1.5 g/kg body weigh is injected intraperitoneally. Blood glucose levels are measured before the glucose injection (0 minutes), as well as at 30, 60 and 90 minutes after the glucose injection, to observe the blood glucose level change curves.

Figures 5A, 5B:
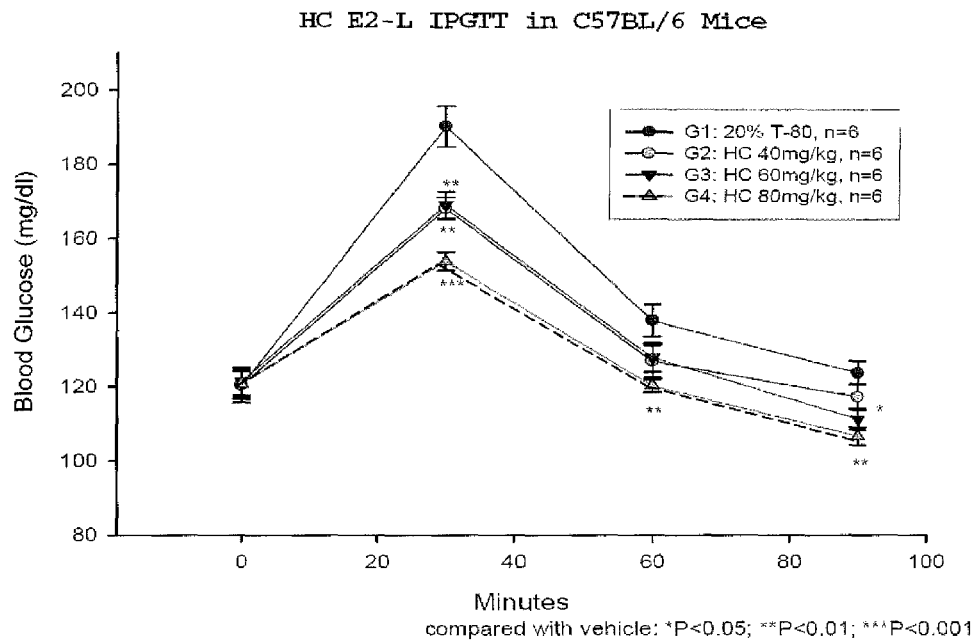
FIG. 5A and FIG. 5B show enhancement of glucose tolerance by compounds of the invention in in vivo tests (mouse IPGTT).

As shown in FIG. 5 and summarized in the Table below, data are expressed as mean±standard error (SEM). P values are calculated using the t test in the Sigma statistical software, wherein $p<0.05$ is considered significant and marked as *; $p<0.01$ is considered highly significant and is marked as ; and $p \leq 0.001$ is considered extremely significant and marked as *.

At 0 minute, 30 minute, 60 minute, and 90 minute time intervals, blood samples are collected to measure the glucose levels (in mg/DL) (see table below), to observe the glucose level change curve. The results show that in the wild ginger flower ethanol extract, the isolated compound (HC E2-L) can significantly reduce blood glucose levels, and its hypoglycemic effects show dose dependence: 41% (40 mg/Kg group), 45% (60 mg/Kg group), and 71% (80 mg/Kg group). These results show that compounds of the invention can improve glucose tolerance (lower spikes of glucose levels after challenges) in patients.

| | Blood glucose concentration (mg/dl) | | | |
|---|---|---|---|---|
| | 0 minute | 30 minute | 60 minute | 90 minute |
| Placebo group | 120.3 ± 4.7 | 190.3 ± 5.5 | 138.0 ± 4.3 | 123.8 ± 3.2 |
| 40 mg/kg group | 120.5 ± 3.8 | 168.2 ± 3.0** | 127.0 ± 4.4 | 117.3 ± 3.4 |
| 60 mg/kg group | 121.5 ± 3.7 | 169.2 ± 3.6** | 128.0 ± 4.0 | 111.3 ± 2.9* |
| 80 mg/kg group | 120.8 ± 3.7 | 154.0 ± 2.5*** | 120.3 ± 1.8** | 106.7 ± 2.5*** |

Advantages of embodiments of the invention may include one or more of the following. Compounds of the invention are GLP-1 potentiators. These potentiators work through the normal GLP-1/GLP-IR mechanism. Because GLP-1 function is glucose dependent and would not over-lower the fasting glucose levels, the functions of this series of compounds would have the same properties—i.e., glucose-dependent. Therefore, they are different from the traditional sulfonylurea compounds and do not cause hypoglycemia—i.e., they do not reduce fasting blood glucose levels in individuals and have less side effects. In addition, these compounds are not peptides. These small molecules would have better pharmacokinetics and longer in vivo half-lives.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A compound for controlling blood glucose level, wherein the compound has a structure shown in Formula I:

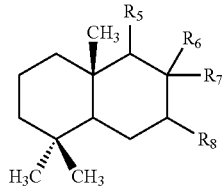

Formula I wherein
$R_8$ is H, —OH, or —O—R';
$R_5$ is $C_2$-$C_4$ alkenyl or $C_7$-$C_{10}$ alkenyl, which is straight-chained or branched and is optionally substituted with one or more substituents selected from —OR', —NR'R", —SR', oxo (=O), thioxo (=S), —CONR'R", —CO$_2$R', or —CR'R"OH, wherein R' and R" are independently H, $C_1$-$C_{10}$ alkyl or $C_2$-$C_{10}$ alkenyl; or $R_5$ is a 5- or 6-membered ring that is a cycloalkyl or cycloalkenyl ring or a heterocyclic ring with one or more hetero atoms selected from N, O, or S, wherein the 5- or 6-membered ring is optionally substituted with one or more substituent selected from —OR', —NR'R", —SR', oxo (=O), thioxo (=S), —CONR'R", —CN, —CO$_2$R', or —CR'R"OH; and
$R_6$ and $R_7$ are independently selected from H (provided that $R_6$ and $R_7$ are not both H), $C_1$-$C_{10}$ alkyl or $C_2$-$C_{10}$ alkenyl, which is straight-chained or branched and is optionally substituted with one or more substituents selected from —OR', —NR'R", —SR', oxo (=O), thioxo (=S), —CONR'R", —CN, —CO$_2$R', or —CR'R"OH, or $R_6$ and $R_7$ jointly form =CH$_2$;
wherein R' and R" are independently H, $C_1$-$C_6$ alkyl, $C_2$-$C_6$ alkenyl, cycloalkyl or $C_6$-$C_{10}$ aryl;
or wherein
$R_7$ is —CHO, and $R_5$ and $R_6$ jointly form a ring, which is a 5 or 6-membered ring made of C, O, N, or S atoms or a combination thereof, wherein the ring has 0 or 1 double bond, and wherein the ring is optionally substituted with one or more alkyl side chains of 1-10 carbons ($C_1$-$C_{10}$), and wherein the ring and/or the one or more alkyl side chains independently are optionally substituted with one or more substituents selected from —OR', —NR'R", —SR', oxo (=O), thioxo (=S), —CONR'R", —CN, —CO$_2$R', or —CR'R"OH.

2. The compound of claim 1, wherein $R_6$ and $R_7$ jointly form =CH$_2$ and the compound has a structure shown in Formula II:

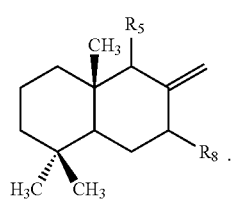

Formula II

3. A method for controlling blood glucose level, comprising administering to a subject in need thereof a compound of formula I shown below and a glucagon-like peptide-1 (GLP-1) receptor ligand,

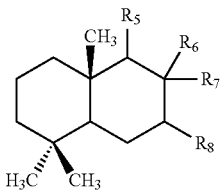

Formula I wherein
$R_8$ is H, —OH, or —O—R';
$R_5$ is $C_1$-$C_{10}$ alkyl or $C_2$-$C_{10}$ alkenyl, which is straight-chained or branched and is optionally substituted with one or more substituents selected from —OR', —NR'R", —SR', oxo (=O), thioxo (=S), —CONR'R", —CN, —CO$_2$R', or —CR'R"OH, wherein R' and R" are independently H, $C_1$-$C_{10}$ alkyl or $C_2$-$C_{10}$ alkenyl; or $R_5$ is a 5-, 6- or 7-membered ring that is a cycloalkyl or cycloalkenyl ring or a heterocyclic ring with one or more hetero atoms selected from N, O, or S, wherein the 5-, 6-, or 7-membered ring is optionally substituted with one or more substituent selected from —OR', —NR'R", —SR', oxo (=O), thioxo (=S), —CONR'R", —CN, —CHO, —CO$_2$R', or —CR'R"OH; and
$R_6$ and $R_7$ are independently selected from H (provided that $R_6$ and $R_7$ are not both H), $C_1$-$C_{10}$ alkyl or $C_2$-$C_{10}$ alkenyl, which is straight-chained or branched and is optionally substituted with one or more substituents selected from —OR', —NR'R", —SR', oxo (=O), thioxo (=S), —CONR'R", —CN, —CHO, —CO$_2$R', or —CR'R"OH, or $R_6$ and $R_7$ jointly form =CH$_2$;
wherein R' and R" are independently H, $C_1$-$C_6$ alkyl, $C_2$-$C_6$ alkenyl, $C_3$-$C_{10}$ cycloalkyl or $C_6$-$C_{10}$ aryl;
or wherein
$R_7$ is —CHO, and $R_5$ and $R_6$ jointly form a ring, which is a 5, 6 or 7-membered ring made of C, O, N, or S atoms or a combination thereof, wherein the ring has 0 or 1 double bond, and wherein the ring is optionally substituted with one or more alkyl side chains of 1-10 carbons ($C_1$-$C_{10}$), and wherein the ring and/or the one or more alkyl side chains independently are optionally substituted with one or more substituents selected from —OR', —NR'R", —SR', oxo (=O), thioxo (=S), —CONR'R", —CN, —CHO, —CO$_2$R', or —CR'R"OH.

4. The method of claim 3, wherein the GLP-1 receptor ligand is GLP-1 or exendin-4.

5. The method of claim 3, wherein the compound and the GLP-1 receptor ligand are administered together.

6. The method of claim 3, wherein the compound is one selected from the following compounds:
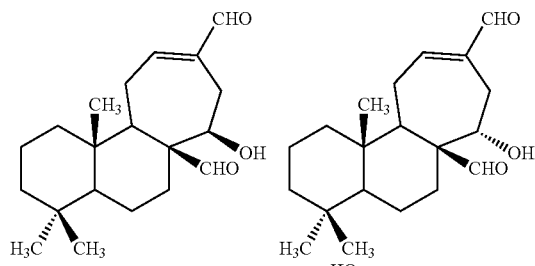
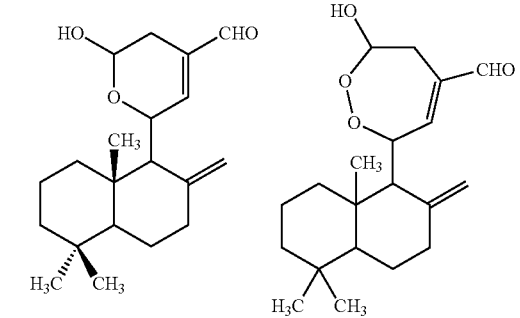
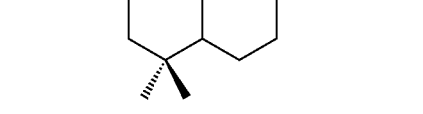
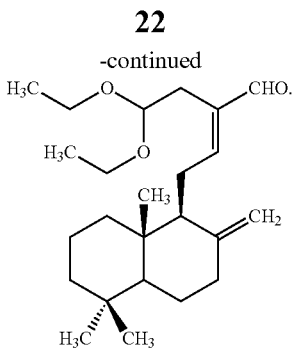
7. The method of claim 6, wherein the compound is
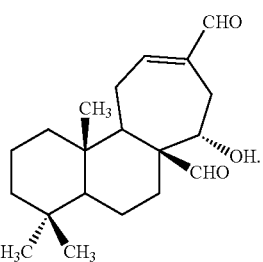
8. The method of claim 6, wherein the compound is
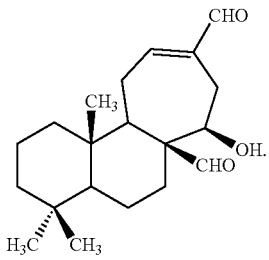
* * * * *